(12) United States Patent
Lange et al.

(10) Patent No.: US 9,289,764 B2
(45) Date of Patent: Mar. 22, 2016

(54) METHOD FOR MIXING AT LEAST ONE SAMPLE SOLUTION HAVING AT LEAST ONE REAGENT, AND DEVICE

(75) Inventors: Berthold Lange, Werne (DE); Christian Schoen, Dresden (DE); Tobias Eichmann, Recklinghausen (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 36 days.

(21) Appl. No.: 13/991,817

(22) PCT Filed: Dec. 13, 2011

(86) PCT No.: PCT/EP2011/072659
§ 371 (c)(1),
(2), (4) Date: Aug. 5, 2013

(87) PCT Pub. No.: WO2012/084615
PCT Pub. Date: Jun. 28, 2012

(65) Prior Publication Data
US 2014/0160877 A1    Jun. 12, 2014

(30) Foreign Application Priority Data

Dec. 20, 2010  (EP) .................................. 10196050
Feb. 11, 2011  (EP) .................................. 11001134

(51) Int. Cl.
*G01N 35/00*     (2006.01)
*B01L 3/00*      (2006.01)
(Continued)

(52) U.S. Cl.
CPC ........... *B01L 3/50273* (2013.01); *B01F 1/0011* (2013.01); *B01F 7/0015* (2013.01); *B01F 7/00033* (2013.01); *B01F 7/00291* (2013.01); *B01F 7/161* (2013.01); *B01F 11/008* (2013.01); *B01F 13/0059* (2013.01); *B01F 15/0205* (2013.01); *B01F 15/0212* (2013.01); *B01L 2200/16* (2013.01); *B01L 2400/0475* (2013.01); *B01L 2400/065* (2013.01); *B01L 2400/0633* (2013.01); *B01L 2400/0683* (2013.01);
(Continued)

(58) Field of Classification Search
CPC .................................................. B01L 3/50273
See application file for complete search history.

(56) References Cited

U.S. PATENT DOCUMENTS 3,780,992  A    12/1973  Nishi
4,612,291  A *  9/1986  Dawes .......................... 436/174
(Continued)

FOREIGN PATENT DOCUMENTS

DE            19900347 A1    7/2000
DE         202004019444 U1    3/2005
(Continued)

OTHER PUBLICATIONS

International Search Report and Written Opinion for PCT/EP2011/072659 mailed Feb. 29, 2012.

*Primary Examiner* — Tony G Soohoo
*Assistant Examiner* — Elizabeth Insler
(74) *Attorney, Agent, or Firm* — Michael P. Morris; Mary-Ellen M. Devlin

(57) ABSTRACT

Methods and apparatus for mixing at least one sample solution with at least one reagent in at least one chamber of a microfluidic cartridge such that at least one reagent (R) is supplied to the sample solution (P) and brought into contact therewith by way of at least one movable component. In this way the loss of sample liquid or analyte can be reduced.

5 Claims, 2 Drawing Sheets

Figure 1:
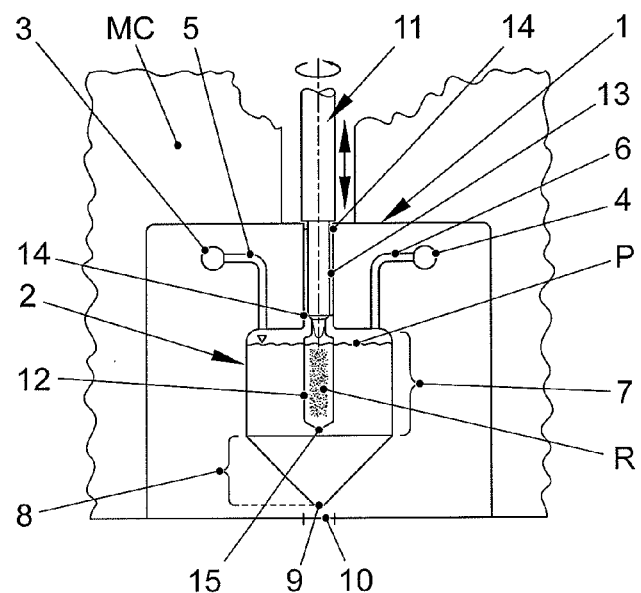

(51) Int. Cl.
  *B01F 1/00* (2006.01)
  *B01F 7/00* (2006.01)
  *B01F 7/16* (2006.01)
  *B01F 11/00* (2006.01)
  *B01F 13/00* (2006.01)
  *B01F 15/02* (2006.01)
  *G01N 35/10* (2006.01)

(52) U.S. Cl.
  CPC ... *G01N2035/1055* (2013.01); *G01N 2035/1058* (2013.01)

(56) References Cited

U.S. PATENT DOCUMENTS

| | | | |
|---|---|---|---|
| 4,874,114 A * | 10/1989 | Guigan | 73/864.11 |
| 4,877,745 A * | 10/1989 | Hayes et al. | 436/166 |
| 5,254,479 A | 10/1993 | Chemelli | |
| 5,443,791 A * | 8/1995 | Cathcart et al. | 422/65 |
| 6,927,045 B2 | 8/2005 | Hadd | |
| 7,258,480 B2 * | 8/2007 | Dunfee et al. | 366/197 |
| 7,473,397 B2 | 1/2009 | Griffin | |
| 9,067,209 B2 | 6/2015 | Squirrell | |
| 2002/0182117 A1 * | 12/2002 | Coassin et al. | 422/100 |
| 2003/0032052 A1 | 2/2003 | Hadd | |
| 2005/0272169 A1 | 12/2005 | Griffin | |
| 2007/0297277 A1 | 12/2007 | Tytar | |
| 2009/0019953 A1 | 1/2009 | Bommarito | |
| 2011/0274585 A1 | 11/2011 | Miyamoto | |
| 2012/0040470 A1 | 2/2012 | Dorn | |
| 2014/0160877 A1 | 6/2014 | Lange | |
| 2015/0125939 A1 | 5/2015 | Squirrell | |

FOREIGN PATENT DOCUMENTS

| | | | |
|---|---|---|---|
| DE | 102009016712 A1 | 10/2010 |
| JP | 05261270 A | 10/1993 |
| JP | 08506893 A | 7/1996 |
| JP | 11510601 A | 9/1999 |
| JP | 2001502793 A | 2/2001 |
| JP | 2003505711 A | 2/2003 |
| JP | 2004537714 A | 12/2004 |
| JP | 2005512071 A | 4/2005 |
| JP | 2005274199 A | 10/2005 |
| JP | 2006313122 A | 11/2006 |
| JP | 2008302322 A | 12/2008 |
| JP | 2009503552 A | 1/2009 |
| WO | 9418564 A1 | 8/1994 |
| WO | 9706437 A1 | 2/1997 |
| WO | 9726539 A1 | 7/1997 |
| WO | 9813684 A1 | 4/1998 |
| WO | 2010064503 A1 | 6/2010 |
| WO | 2012084615 A1 | 6/2012 |

* cited by examiner

METHOD FOR MIXING AT LEAST ONE SAMPLE SOLUTION HAVING AT LEAST ONE REAGENT, AND DEVICE

The invention relates to a method for mixing at least one sample solution with at least one reagent in at least one chamber of a microfluidic cartridge and to a device for carrying out the method.

Bio- and gene technology has become enormously important in recent years. A basic task of this technology is to detect specific biological substances (analytes) in fluid samples. By detecting analytes in fluid samples, for example in a sample of a patient's blood, it is possible among other things to detect pathogens, thus making it easier for the doctor to arrive at a diagnosis and thereby also promoting rapid treatment and infection control.

Increasingly, microfluidic components or microfluidic cartridges are used in bio- and gene technology.

Microfluidic cartridges are often used in the form of single-use tests, generally using so-called Lateral Flow Cartridges, the components of which have longitudinal and width dimensions ranging from a few millimeters to several centimeters.

In order to carry out tests, as a rule an analytical liquid (e.g. blood, urine or saliva) that is to be tested is supplied by suitable means to a microfluidic cartridge equipped with a biosensor (biochip). Sample solution is added to the cartridge before or after the cartridge is inserted in a suitable analyser.

The term "micro" is intended to imply that at least one of the channels and/or cavities (chambers) present has a dimension on the micron scale, i.e. measuring less than one millimeter, at least in one geometric direction.

By the term "microfluidic" is meant that a pressure-induced and/or capillary flow of liquid takes place through and within the microchannels and/or microcavities.

By a "microfluidic component" is meant a component which comprises at least microchannels or microcavities of this kind for the storage and transporting of liquids or fluids.

A "microfluidic cartridge" is a device (possibly consisting of a number of microfluidic components) for the analysis of liquids.

It is often difficult to detect low concentrations of biological and inorganic substances in biological samples. The tests (assays) for this type of detection in microfluidic cartridges generally involve several steps.

In modern microfluidic cartridges there is a need to shorten the measuring time between the application of the sample solution and the eventual appearance of the measured value. In addition the trend is towards obtaining reliable measurements with ever smaller amounts of sample solution.

When measurements are carried out in a microfluidic cartridge, normally a small amount of a sample solution is passed through one or more chambers which contain reagents or conditioning agents that serve to prepare the sample for being brought into contact with the reagents. The sample solution is therefore generally passed sequentially through different chambers connected by microchannels, through which the sample solution is moved by capillary forces or an applied force such as for example centrifugal force or an applied pressure differential.

The detection of an analyte being sought ultimately takes place in the microfluidic cartridge by means of the specific binding or reaction of the analyte present in the sample solution with a so-called reagent (identification reaction). Generally, the specificity of the identification reaction makes it possible to determine, qualitatively or quantitatively, even analytes in complex samples such as body fluids, for example, with no or only minimal purification beforehand.

In the microfluidic cartridges the reagents are usually immobilised in a certain region or in a certain chamber. In the course of the fluidic procedure, the sample solution in liquid form is supplied to these reagents from another region of the microfluidic cartridge so as to dissolve the reagents and carry out the identification reaction. However, as the sample solution is conveyed from chamber to chamber, losses of the sample solution may occur, as for example chambers and channels cannot be adequately emptied during the capillary transport. This is particularly critical with the small sample volumes of less than 10 microliters that are now the norm.

Moreover, the transporting of the sample solution may result in a falsification of the measuring result due to non-specific binding or adhesion, for example.

In non-specific binding the analytes bind with different substances than the intended ones and are thus lost as reactive material. In adhesion the analytes of interest are partly lost as a result of their accumulation on surfaces/walls.

From DE 2009 016 712 A1 a microfluidic cartridge (single-use test cassette) for the bioassay of analytes and a device in which the microfluidic cartridge is inserted are known.

The microfluidic cartridge described therein has a structured body in which cavities interconnected by channels are provided. An inlet is provided for introducing a sample solution containing an analyte, as well as a reagent chamber which holds one or more reagents for reacting with the analyte or for mixing with the sample solution. In addition a detection chamber is provided in which a signal for the detection or quantitative analysis of the analyte is detected. The detection chamber comprises a window for detecting a signal. The reagents are deposited in the reagent chamber in dry form, the sample solution being transported within the microfluidic cartridge by jets of air of precisely defined volume and timing.

All in all this is intended to provide an inexpensive, storable and easily operated means for carrying out biochemical test procedures for the purpose of detecting analytes qualitatively and/or quantitatively. Moreover, the specification also refers to the control of the reaction conditions, particularly the volumes and times, as well as optimum mixing of the sample solution and reagents.

However, ultimately it does not depart from the known method of transporting the sample solution to the reagents within a microfluidic cartridge.

The aim of the present invention is to provide a method according to the preamble of claim 1 in which the above-mentioned disadvantages of the prior art are mitigated.

A further aim of the present invention is to provide a suitable device for carrying out the method.

With respect to the method, this aim is achieved by the characterising features of claim 1. As for the device the aim is achieved by the features of claim 11.

With regard to the method the invention starts from a method for mixing at least one sample solution with at least one reagent in at least one chamber of a microfluidic cartridge.

According to the invention it is provided that at least one reagent is supplied to the sample solution and brought into contact therewith by means of at least one movable component.

The reagent is this introduced into a chamber in which the sample solution is already present. The sample solution therefore no longer has to be moved within the fluidic network, thus minimising the losses of sample and analyte.

For example it may be envisaged that two successive reactions of a sample solution each require one reagent for an assay.

According to the prior art this would require two chambers, each containing one of the reagents suitably immobilised. First of all, the sample solution has to be conveyed into the chamber containing the first reagent. The sample solution then reacts with this reagent and all the (pre-processed) liquid is then conveyed by capillary forces or pressure into the next chamber, so as to react with the second reagent.

In the method according to the invention it is now possible to have both reactions take place in one and the same chamber (without any transporting of the sample solution). For example, the first reagent could already be deposited in the chamber and react with the sample solution once it is introduced. After a certain length of time the second reagent could then be added to the sample solution in the chamber and brought into contact therewith by means of the movable component.

However, it is also possible to carry a plurality of reagents on the movable component simultaneously. For example, two different reagents could be stored separately from one another on the movable component, e.g. on its front and back. This may be very advantageous for certain applications.

However it is also possible to use a plurality of different components each of which carries one reagent, for example, and is introduced into the sample solution as required.

If the movable component is moved towards the sample solution in a substantially translational movement, this simplifies the method and the device for carrying out the method may be kept comparatively simple in its construction.

In order to achieve a rapid and high-quality identification reaction, thorough mixing of the sample solution with the reagents is desirable. It is therefore highly beneficial if the movable component performs a rotary movement during contact of the reagent with the sample solution. Good mixing can be further promoted if the movable component performs an oscillating movement or a circular movement at least during the contact of the reagent with the sample solution. Of course, it is naturally possible and certainly advantageous for the above-mentioned movements to be superimposed on one another.

It is expedient if at least the part of the movable component on which the reagent is held is immersed in the sample solution in such a way that the reagent is completely surrounded by the sample solution.

The reagent or reagents may advantageously be immobilised on the movable component by drying. This may be done conventionally, for example, or by freeze-drying. The advantage of freeze-drying is that the dried reagent or reagents is or are immobilised in the form of a porous mass which forms a large surface area and therefore dissolves quickly on contact with the sample solution.

It may be envisaged that before the reagent is contacted with the sample solution the movable component opens up at least one closed access to the chamber. In this way the chamber is protected from contamination from the outside and a sample solution that has already been introduced into the chamber is unable to get out and thus lead to contamination of the environment or of equipment, even during the transporting of for example a microfluidic cartridge containing the chamber.

To improve the mixing of the sample solution and reagent it may be very expedient if the movable component is of a spatula-like configuration. Moreover, the surfaces of a spatula comprise suitable areas for the depositing of reagents.

However, it is naturally also possible to configure the movable component differently. For example, it could also be of spiral configuration, so as to achieve a mixing effect similar to that obtained with a mixer.

The invention also, however, relates to a device for carrying out the method according to the invention. The device according to the invention comprises at least one microfluidic cartridge with at least one chamber for receiving a sample solution, the chamber containing at least one access into which a movable component carrying at least one reagent can be introduced.

A device of this kind enables the method to be carried out easily.

According to a further feature of the device according to the invention the at least one access may be closed off such that it can be pierced by the movable component. The access may for example be sealed by a flexible or rubber-like film. In this way, a certain sealing action can be achieved even after the closure has been pierced, as the flexible film, having been pierced, fits snugly around the movable component again.

The movable component is advantageously spatula-like in configuration. For one thing, the spatula surface can significantly increase the mixing of the sample solution and reagents, for example during a rotary movement of the movable component, and for another thing it is easy to deposit reagents on a spatula-like surface. Finally, it is thus certainly possible to use standard laboratory-type spatulas as the movable component, thus reducing the costs of the device accordingly.

The microfluidic component of the device may be part of a microfluidic cartridge. Microfluidic cartridges constitute a convenient option for carrying out biotechnical arrays.

To optimise the proper use of the microfluidic cartridge and the evaluation of the assay, it may be envisaged to have the microfluidic cartridge operatively connected to an analyser. Thus, even an unpractised user who does not have daily experience of tests of this kind can carry out an assay correctly and reproducibly.

It may be advantageous if the movable element is movably connected to the microfluidic cartridge. The movable component and the microfluidic cartridge may be supplied as a (retail) unit, so to speak. Then the user has only to take from the packaging a unit comprising a cartridge and corresponding reagents according to the array that is to be carried out, supply the corresponding sample solution and then connect the cartridge to the analyser to start the array and evaluate it.

Alternatively it would also be possible to connect the movable component movably to the analyser. In this case a kind of magazine for a plurality of movable components, each having reagents for different arrays, could also similarly be provided in the analyser, for example.

For fully automating the array it is very useful if the movable component is moved by means of at least one actuator of the analyser.

Figure 2:
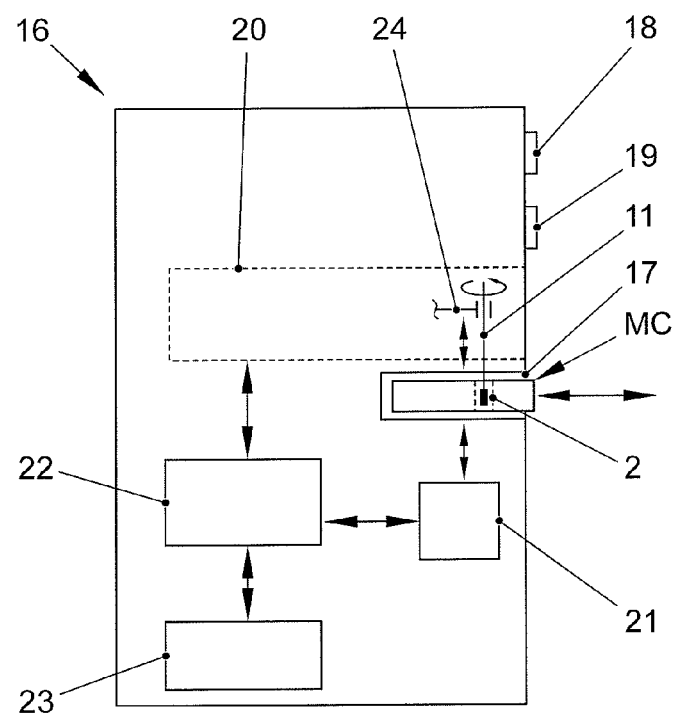
Figure 3:
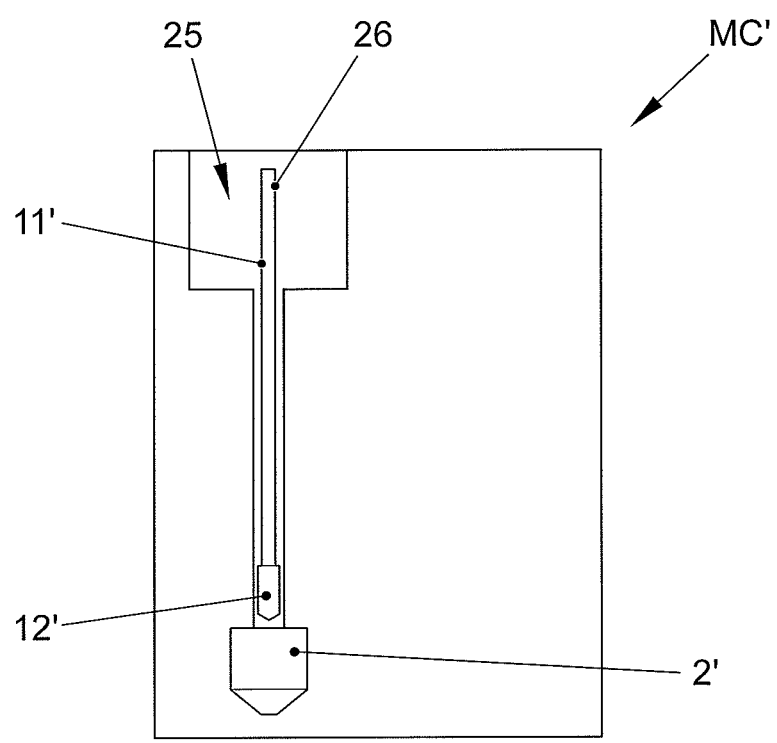

Further features and advantages of the invention will become apparent from some embodiments by way of example, as will be illustrated in more detail by means of the attached Figures, wherein FIG. 1 is a schematic representation of a first embodiment of the invention, showing a detail of a microfluidic cartridge, FIG. 2 is a schematic representation of an analyser into which the microfluidic cartridge according to FIG. 1 is introduced and FIG. 3 shows a second embodiment of the device according to the invention.

Reference will be made first of all to FIG. 1.

This shows a microfluidic cartridge MC with a microfluidic component 1 (biochip). The microfluidic component 1 comprises an assay chamber 2 for carrying out a bioassay. A corresponding sample solution P can be supplied to the assay chamber 2 or discharged therefrom through a fill opening 3 and a vent opening 4, which are connected to the assay chamber 2 via corresponding channels 5 and 6.

The assay chamber 2 comprises a first chamber region 7 of constant cross-section in the millimeter range and a second chamber region 8 which tapers conically towards a measuring surface 9. The measuring surface 9 is transparent and is used for the optical read-out of an identification or immune complex (not shown in detail) formed after a specific identification or immune reaction and immobilised in the region of the measuring surface. The conical convergence of the second chamber region 8 towards the measuring surface 9 makes measurement easier, even if only comparatively few antibodies and immobilising means are available.

The measurement is carried out using an optical measuring unit 21 which has optical access to the measuring surface 9 via a window 10 (cf. also FIG. 2).

FIG. 1 also shows that a rod-shaped reagent carrier 11 with a spatulate end 12 has been immersed in the sample P. The spatulate end 12 is provided with reagents R on its front and on its back (not shown). Thus, for example, capture antibodies are contained on the front and detection antibodies are present on the back of the spatulate end 12. The reagents R are preferably immobilised on the spatulate end 12 by freeze-drying.

Overall, the reagent carrier 11 thus has a substantially rod-like appearance, and can be inserted with its spatulate end 12 in the assay chamber through a channel- or groove-like access 13 located in the microfluidic component 1.

Before the reagents R are supplied by means of the reagent carrier 11 the assay chamber 2 is sealed off by means of two film-like closures 14. This reduces the risk of contaminating the assay chamber 2 or the sample solution P or the environment. By keeping a stock of several film-like closures 14 this can be ensured even if one of the closures 14 is damaged.

In order to reach the assay chamber 2, the reagent carrier 11 has to pierce the two film-like closures 14 with its spatulate end 12. To assist this the spatulate end 12 is provided with a point 15 for this purpose. The film of the closures 14 may conveniently be made of a resilient material to promote the sealing action of the closures 14 even after they have been pierced.

In FIG. 1 the reagent carrier 11 has already been inserted with its spatulate end 12 into the assay chamber 2 far enough for the reagents R to be fully immersed in the sample solution P.

The introduction of the reagents R into the sample solution P is thus achieved by a simple translational movement of the reagent carrier 11 in the direction of the sample solution P or the assay chamber 2. In addition, arrows are provided to indicate that the reagent carrier may perform a rotary stirring movement during the mixing of the reagents R with the sample solution P. As a result of these additional movements of the reagent carrier 11 the mixing of the reagents R with the sample solution P can be significantly improved.

The shape of a spatulate reagent carrier 11 has the advantage that in some cases it is possible to use a conventional disposable spatula from the laboratory supplies at correspondingly low cost. However, other forms of the reagent carrier 11, and particularly its end 12, are also conceivable. Thus, the end 12 might also be triangular in cross-section, for example, so that one reagent can be immobilised on each surface, i.e. a total of three reagents may be immobilised separately from one another. In the case of a rectangular or star-shaped cross-section even more reagents could be deposited.

A spiral configuration comparable with that of a mixer is also possible, for example, and would achieve a good mixing effect.

FIG. 2 shows in highly diagrammatic form an analyser 16 in the form of a bench apparatus into which the microfluidic cartridge MC can be inserted after the introduction of the sample solution P, for carrying out the bioassay and the corresponding evaluation.

The microfluidic cartridge MC is preferably an injection-moulded component.

The apparatus according to the invention is then used as follows:

The microfluidic cartridge MC is taken out of the packaging and the sample solution P is supplied to the assay chamber 2 in a suitable manner. This may be done for example through a corresponding sample application region by the patient himself or by a doctor. The corresponding fill openings in the microfluidic cartridge MC are then suitably sealed off, for example by means of an adhesive tab. Then the microfluidic cartridge MC is pushed into a corresponding receiving slot 17 of the analyser 16.

The analyser 16 has a start button 18 for starting the particular bioassay that is to be selected using a programme selecting switch 19. Moreover, the analyser 16 is provided with an optical measuring unit 21 for carrying out the measurement, a control and evaluating unit 22 and an output unit 23 (for example in the form of a display).

Once the array that is to be carried out has been selected using the programme switch 19 and the start button 18 has been activated, the analysis is started and the control and evaluating unit 22 operates actuators 24 provided in the analyser 16 at the right time depending on the prescribed sequence of events for the bioassay and move the reagent carrier towards the assay chamber 2 as described previously. The actuators 24 are configured so as to allow a rotary movement of the reagent carrier 11 as well as a purely translational movement.

Moreover, FIG. 2 also shows that the analyser 16 may be equipped with a magazine 20 for a plurality of reagent carriers 11. It would be possible for each reagent carrier 11 to be provided with different reagents R depending on the bioassay to be selected using the programme selecting switch. After the bioassay has been chosen accordingly, the particular reagent carrier 11 required is then selected by the analyser 16 and supplied to the assay chamber 2.

As shown highly diagrammatically in FIG. 3, it would naturally also be possible to provide a (retail) unit consisting of a microfluidic cartridge MC' and a reagent carrier 11'. Each unit of this kind could be associated with a particular bioassay to be carried out. After the unit had been unpacked and a sample solution had been introduced into an assay chamber 2' in an analogous manner to that described, the unit could then in turn be inserted in a correspondingly configured analyser (not shown), while the reagent carrier 11' could in turn be moved on a separate end region 26 (located within a recess 25 provided in the cartridge MC') by means of suitable actuators of the analyser or introduced into the assay chamber 2'.

LIST OF REFERENCE NUMERALS 1 microfluidic component
2,2' assay chamber
3 fill opening
4 vent opening
5 feed channel
6 discharge channel
7 first chamber region 8 second chamber region
9 measuring surface
10 window
11,11' reagent carrier
12,12' spatulate end
13 access
14 film-like closure
15 point
16 analyser
17 receiving slot
18 start button
19 programme selecting switch
20 magazine for reagent carriers
21 laser and measuring unit
22 control and evaluating unit
23 output unit
24 actuators
25 recess for actuators of the analyser
26 end region of the reagent carrier as a point of engagement for actuators
MC, MC' microfluidic cartridge
P sample solution
R reagent

The invention claimed is:

1. A method for mixing at least one sample solution (P) with at least one reagent (R), the method comprising:
   providing a microfluidic cartridge (MC) having: (i) at least one chamber (2,2') in which the sample solution (P) is disposed, (ii) an access (13) extending from an exterior of the microfluidic cartridge (MC) into fluidic communication with the chamber (2,2'), and (iii) a seal (14) disposed within the access (13) closing off the fluidic communication with the chamber (2,2'),
   inserting the microfluidic cartridge (MC) into an analyser (16) such that the access (13) is in registration with at least one movable component (11,11'), each of which includes a distal end having at least one reagent (R) located thereon,
   supplying the at least one reagent (R) to the sample solution (P) and bringing the at least one reagent (R) into contact therewith by moving the at least one movable component (11,11') through the access (13) so as to pierce the seal (14) and extend into the chamber (2,2'),
   activating the movable component (11,11') to perform a rotary movement at least during the contact of the reagent (R) with the sample solution (P),
   activating the movable component (11,11') to perform an oscillatory movement at least during the contact of the reagent (R) with the sample solution (P), and
   activating the movable component (11,11') to perform a circular movement at least during the contact of the reagent (R) with the sample solution (P).

2. The method according to claim 1, wherein a plurality of reagents (R) are held on the movable component (11,11').

3. The method according to claim 1, wherein the movable component (11,11') is immersed in the sample solution (P), at least with the part (12,12') on which the reagent (R) is held, such that the reagent (R) is completely surrounded by the sample solution (P).

4. The method according to claim 1, wherein the at least one reagent (R) is immobilized on the movable component (11,11') by drying.

5. The method according to claim 1, wherein the movable component (11,11') is of spatulate (12,12') configuration.

* * * * *